US012646592B2

(12) United States Patent
Lin et al.

(10) Patent No.: US 12,646,592 B2
(45) Date of Patent: Jun. 2, 2026

(54) MOLECULAR FORCE FIELD MULTI-OBJECTIVE FITTING ALGORITHM LIBRARY AND WORKFLOW

(71) Applicant: SHENZHEN JINGTAI TECHNOLOGY CO., LTD., Guangdong (CN)

(72) Inventors: Hongrui Lin, Guangdong (CN); Mingjun Yang, Guangdong (CN); Chunwang Peng, Guangdong (CN); Chunan Wu, Guangdong (CN); Jian Ma, Guangdong (CN); Shuhao Wen, Guangdong (CN); Lipeng Lai, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 1196 days.

(21) Appl. No.: 17/432,092

(22) PCT Filed: Jul. 8, 2020

(86) PCT No.: PCT/CN2020/100813
§ 371 (c)(1),
(2) Date: Aug. 19, 2021

(87) PCT Pub. No.: WO2022/006771
PCT Pub. Date: Jan. 13, 2022

(65) Prior Publication Data
US 2022/0189586 A1 Jun. 16, 2022

(51) Int. Cl.
G16C 10/00 (2019.01)
G16C 20/70 (2019.01)
(52) U.S. Cl.
CPC ............. G16C 10/00 (2019.02); G16C 20/70 (2019.02)

(58) Field of Classification Search
CPC .......... G06F 30/00; G16C 10/00; G16C 20/70
(Continued)

(56) References Cited

U.S. PATENT DOCUMENTS 5,612,894 A * 3/1997 Wertz ...................... C07K 1/00
703/2
2005/0123993 A1 6/2005 Brunner et al.

FOREIGN PATENT DOCUMENTS

CN 101131707 A * 2/2008
CN 103646178 3/2014
(Continued)

OTHER PUBLICATIONS

Sami, Selim et al., "Q-Force: Quantum Mechanically Augmented Molecular Force Fields", 2021, Journal of Chemistry Theory and Computation, 17, American Chemical Society. (Year: 2021).*
(Continued)

*Primary Examiner* — Cedric Johnson
(74) *Attorney, Agent, or Firm* — MUNCY, GEISSLER, OLDS & LOWE, P.C.

(57) ABSTRACT

The present invention provides a molecular force field multi-objective fitting algorithm library and the workflow, including: FFOptIterator as the main module for input and output and force field parameter training iteration; Energy-Calculator module used for MM energy and energy derivatives calculation for the required value of each iteration in the optimization algorithm; the PropertyEstimator module used for the thermodynamic property calculation based on the MD simulation. Wherein, when initializing the FFOptIterator and EnergyCalculator objects, the user specifies the training force field parameters, adjustable parameter ranges, system setting arguments, and MD simulation parameters. The invention is suitable for the related applications of molecular force field training and verification, and implement the framework for different training targets, the (Continued)

> Supported Target Properties

1. Conformational energy (QM)
2. Dimer interaction energy (QM)
3. Crystal Lattice Parameters (Exp)
4. Liquid Density (Exp)
5. HOV (Exp)
6. HOS (Exp)
7. HOF (Exp)

> General Target Functions $$T(\lambda) = \sum_i w_i (P_i^{MM}(\lambda) - P_i^{QM/Exp})^2$$

The exact form would be different for each target properties!

MM energy physical and chemical properties calculation

Target Data (QM or Experimental)

Input data:
Molecular system
Force field
Training set
Target type

Optimize Target Function
Update Force Field parameters
(L-BFGS-B)

Target Function

Converged?
NO
YES

Optimized Parameters prediction of different molecular physical properties, the compatibility and conversion of force field parameters in different formats, integration of multi-objective optimization, result analysis and graphing, etc.

8 Claims, 2 Drawing Sheets

(58) Field of Classification Search
USPC ............................................................. 703/2
See application file for complete search history.

(56) References Cited

FOREIGN PATENT DOCUMENTS

| | | | | |
|---|---|---|---|---|
| CN | 104715096 | 6/2015 | | |
| CN | 107025383 | 8/2017 | | |
| CN | 111863141 A * | 10/2020 | ............ | G16C 10/00 |
| WO | WO-2024238248 A1 * | 11/2024 | | |

OTHER PUBLICATIONS

Grimme, Stefan, "A General Quantum Mechanically Derived Force Field (QMDFF) for Molecules and Condensed Phase Simulations", Aug. 25, 2014, Journal of Chemistry Theory and Computation, 10, American Chemical Society. (Year: 2014).*

"International Search Report (Form PCT/ISA/210) of PCT/CN2020/100813," mailed on Apr. 8, 2021, pp. 1-5.

"Written Opinion of the International Searching Authority (Form PCT/ISA/237) of PCT/CN2020/100813," mailed on Apr. 9, 2021, pp. 1-5.

* cited by examiner

MOLECULAR FORCE FIELD MULTI-OBJECTIVE FITTING ALGORITHM LIBRARY AND WORKFLOW

CROSS-REFERENCE TO RELATED APPLICATION

This application is a 371 of international application of PCT application serial no. PCT/CN2020/100813, filed on Jul. 8, 2020. The entirety of the above mentioned patent application is hereby incorporated by reference herein and made a part of this specification.

TECHNICAL FIELD

The invention pertains to the field of molecular force fields, and in particular relates to a molecular force field multi-object fitting algorithm library and a workflow.

BACKGROUND TECHNIQUE

Molecular Dynamic Simulations have been widely used in various fields of computational biology, chemistry, and materials science. The training and verification of Molecular Forcefields, and the quality evaluation of parameters have become one of the current research focuses on the calculation of properties of small molecule drugs. The molecular force field is the most basic prerequisite for molecular dynamics simulation. At present, when studying molecular simulations involving small molecules, it will involve the assignments of force field parameters, and each step of calculation and iteration is performed based on the energy calculated by the force field.

The current force field parameter development tools mainly have the following defects:

1. It is mostly implemented as a command line tool, and the detailed implementation often involves multiple programming languages, multiple different software packages, file formats, etc., resulting in more dependencies, difficult installation and compilation, and difficult in use.
2. The fitting targets provided are limited, mostly limited to the energy or structure of the intermolecular quantum mechanics (QM) calculation, less involving various properties dominated by intermolecular interaction, and lack of user-definable multi-target fitting functions.
3. The detailed implementations are often deeply bound to the process, lack of modularity, process parameter interface, etc.; users often have to manually modify various input files, or even directly modify the source code, in order to achieve the scientifically expected functions. This makes it difficult to use and difficult to develop.

SUMMARY OF THE INVENTION

In order to solve the above technical problems, the present invention provides a molecular force field multi-objective fitting algorithm library, which has the following main functions:

The implemented target types include: conformational energy, dimer interaction, crystal lattice parameters, liquid density, heat of vaporization (HOV), heat of sublimation (HOS), heat of fusion (HOF) and other properties for the development of force field parameters, and support user-defined multi-objective fitting function.

The specific technical solution is: a molecular force field multi-objective fitting algorithm library, including:

A FFOptIterator (Force Field Optimization Iterator) module for input and output of system settings and training iterations for force field parameters;

An EnergyCalculator (energy calculator) module, for molecular mechanics (MM) energy and energy derivatives calculation, and calculates the target function value for each iteration of the optimization algorithm;

A PropertyEstimator (Property Estimator) module, for calculating thermodynamic properties based on molecular dynamics (MD) simulation.

Wherein, when initializing the FFOptIterator and EnergyCalculator objects, the user specifies the force field parameters to be trained, adjustable parameter ranges, algorithm flow parameters, and MD simulation parameters.

This algorithm library is compatible with mainstream force field file formats such as CHARMM, AMBER, GROMACS, and is based on ParmEd and OpenMM for MD simulations.

Wherein, the FFOptIterator module is the main module of XFFOpt. CHARMM (Chemistry at HARvard Macromolecular Mechanics) is a commercial software for molecular dynamics simulation. The molecular force field used is the CHARMM force field, which has a file format exclusive to the software.

AMBER is a more popular molecular dynamics simulation software nowadays because of its better GPU support, and has a wide range of applications in the field of simulation and calculation of biological macromolecules. The molecular force field it uses is the AMBER force field, which has a file format exclusive to the software.

OpenMM is a high-performance toolkit for molecular simulation. It has Python and C++ APIs and used as a library or application being part of the simTK tool suite for biomolecular simulation, natively supports GPU as a computing platform, so it has a great advantage.

Preferably, MM calculation supports GPU operation; supports simultaneous training of multiple molecules, crystal polymorphs, and multiple force field parameter types.

The present invention adopts the above technical solutions, and its advantage is that the previous molecular force field fitting algorithm library basically does not use OpenMM, so most of it does not support GPU scheduling. This algorithm library relies on OpenMM, and OpenMM's own MM calculations all support GPU scheduling, so the XFFOpt algorithm library can also support GPU calculations. Multiple target force field parameters (FFPs) fitting, consideration of different optimization strategies, as well as crystal polymorphs, etc. are included in our design of XFFOpt architecture, also belonging to the invention, and the details have been described in the process below.

Preferably, in addition to the MD simulations and numerical optimization calling OpenMM and Scipy interfaces, the entire code of this algorithm library is implemented in Python, and SDK is provided. Users can perform secondary development and application of various research and development codes based on the API interfaces of this algorithm library. Only rely on open source third-party algorithm libraries, and follow the principle of minimal dependence. In addition to relying on the mainstream algorithm libraries ParmEd and OpenMM in computational chemistry, it does not rely on any redundant niche third-party packages.

Correspondingly, the present invention also provides a working method of a molecular force field multi-target fitting algorithm library, including the following steps:

Step A: Select the target of parameters for fitting, generate the corresponding QM dataset or collect the corresponding experimental data;

Step B: Perform initial MD simulation and calculation for a specified system and dataset;

Step C: Compare the initial target value calculated by MM with the QM or experimental target value, and calculate the corresponding target function according to the target type, and calculate the derivatives/gradient of the target function with respect to the training parameters;

Step D: Optimize the target function according to the calculated target function and its derivative to obtain an initial force field parameter value in a next iteration, wherein the current algorithm used is the L-BFGS-B method;

Step E: Judge whether the target function reaches the convergence criterion according to the convergence condition; if yes, stop the optimization iteration; if not, perform the next round of MM calculation according to the force field parameter value of the current optimization iteration, and calculate the target function and derivative based on this calculation, and optimize the value of the target function for subsequent iterations until convergence.

Preferably, in the step A, the MD input file corresponding to the system is generated and contains information such as molecular topology, molecular force field parameters being used, etc.; specifies the force field parameters that need to participate in training, such as: bond, angle, dihedral, improper dihedral, charge, Van der Waal, etc.

Preferably, in the step B, the items of the initial MM simulation and calculation include MM energy calculation and prediction of various thermodynamic properties, such as liquid density, crystal lattice parameters, HOV, HOS, HOF, etc.

Preferably, in the step C, the target function is generally the square difference between the MM calculation value and the target value, and the details may be different according to different training target types. The derivative of the target function is calculated analytically by using a equations similar to the ForceBalance method. For different thermodynamic properties, this equation will be different.

Preferably, in the step D, a form of the general target function is:

$$T(\lambda) = \sum_i w_i \left( P_i^{MM}(\lambda) - P_i^{QM/Exp} \right)^2.$$

Wherein, T is the target function value, 2 is a parameter specified by the force field involved in the training, i is an index number of the training dataset, w is the weight of the training goal occupied, P is the target value of MM calculation and QM/Experiment. Specifically, it is the intermolecular conformational energy, dimer interaction, liquid density, crystal lattice parameters, HOV, HOS, HOF, etc.

Correspondingly, the present invention also provides a workflow implementation of the algorithm library, including the following steps:

Step (1): Read the initial MD input file, target type, training set system, configuration, QM or experimental target value, force field parameters to be trained, range of the force field parameters prepared by user, and use the FFOptIterator module as a container to perform various parameter calculations and system operations;

Step (2): Call the iterator of the FFOptIterator module, calculate the MM target value for the system under all target attributes, all MM energy related calculations are completed by an Energy Calculator module, calling an OpenMM Python API (OpenMM Python application program interface); for conformational energy (Conformational energy), develop energy calculation of various conformations scan based on a CustomCompoundForce (customized intramolecular force object) of OpenMM.

Step (3): After the systems contained in each target type have calculated the corresponding MM calculations, calculate the derivatives of the force field parameters between the target function and the ForceBalance target function in the specific form of the respective target function. Finally, integrate the system under all target types, combined weightings of the settings, calculate the total target function and the corresponding gradient, and as the input of the L-BFGS-B optimizer.

Step (4): Call the Fortran L-BFGS-B subroutine inside Scipy, use the above input to optimize the force field parameters, and perform one round of iteration. Check whether the convergence condition of the target function is reached. If not, use the updated force field parameters to edit all systems with ParmEd API (ParmEd Python application program interface), and build the input metadata objects for the next round of MM calculations.

Step (5): Perform the next round of MM calculation iteration, and repeat the above steps to optimize the force field parameters until the target function converges. Under normal circumstances, the number of iterations of the system with the goal of QM energy is about 50-100 rounds, and the number of iterations of the system with the calculation of thermodynamic physicochemical properties as the goal is 8-15 rounds.

Step (6): After the force field parameters being optimized and converged, visualize the output of the force field parameter files and the optimization process according to user operations. The output of parameter files is currently mainly in AMBER mol2 and frcmod formats, and subsequent system modeling in AMBER format can be directly carried out, which is very convenient for the use of MD simulation. In the visualization part, according to the target type specified by the user, the target calculation value comparison before and after the force field parameter optimization and the optimization iterative process of the target function can be constructed from the returned object.

Preferably, in the step (1), the system preparations and parameter modification functions are achieved by the system editing functionalities of the ParmEd object. The FFOptIterator module is designed to be compatible with the input of multiple molecules, crystal polymorphs, and multiple sets of training force field parameters, and includes the structure in the attributes of different target types. The initialized FFOptIterator module completes all system preparations before optimization iterations.

Preferably, in the step (2), for the dimer interaction energy, the calculation of the intermolecular potential energy is developed based on CustomNonbondForce, wherein the van der Waals term adopts the lorentz-berthelot combination rule. For the rest of the thermodynamic properties, use OpenMM to perform conventional isothermal-isobaric (NPT) molecular dynamics simulations. The detailed simulation parameters are set by the user, and the simulation length is set to be long enough to allow the results of the calculation of each property to converge. After the simulation is completed, call the Property Estimator to calculate the thermodynamic properties, such as volume, crystal lattice parameters, HOV, HOS, HOF, etc.

This algorithm library is mainly used for customized force field parameter training, especially for various properties dominated by intermolecular interactions. It is used to parameterize the specialized force field of protein-drug molecule binding and the customized force field development and verification in morphology prediction, etc.

The present invention brings the following effects:

1. Implemented the unified architecture framework of FFPs development tools, with ease of use and very high scalability.

2. Implemented the automatic iteration and analysis of the parameter training protocol, and support the simultaneous optimization of multi-objective, multi-system, and crystal polymorphs.

3. It does not rely on any external binary MD software, and all third-party algorithm libraries are equipped with Python API (Python Application Programming Interface), so it is compatible with various mainstream MD file formats.

4. Implemented the target functions for various type of training targets, and property prediction that supports the interaction of various types of molecules as the basis for force field parameter training.

5. Support users to specify different training parameter combinations, custom force field parameter training ranges, input detailed workflow parameters, MD simulation parameters, etc., so as to be compatible various customized force field fitting strategies according to user needs.

6. This algorithm library supports GPU computing, and provides python SDK, which can directly call the Python API of the corresponding function, and is convenient for analysis and interactive operation process, and can add required analysis code and secondary development to the process. At the same time, background calls are supported, and tasks can be submitted via command lines.

7. The invention is suitable for the related applications of molecular force field training and verification, and implements the framework for different training targets, the prediction process of different properties, the compatibility and conversion of force field parameters in different formats, the integration of multi-objective optimization, the analysis of results, and the visualization.

DETAILED DESCRIPTION

Figure 1:
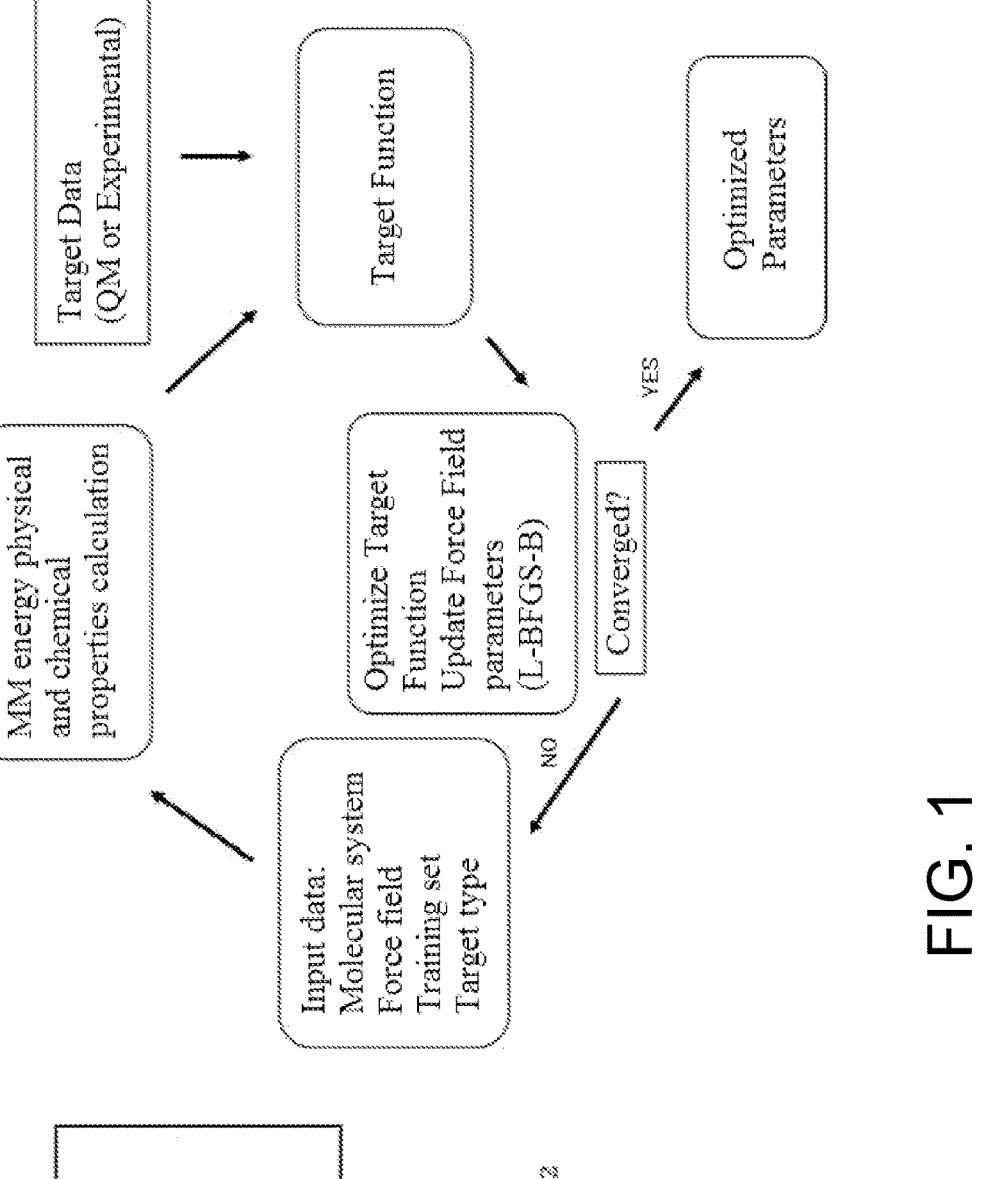
FIG. 1 is principle and flow chart of force field parameter development according to an embodiment of the present invention.

The implementation of the present invention will be further described in detail below with reference to the drawings:

The principle and process of force field parameter development used and implemented by the XFFOpt algorithm library are shown in FIG. 1:

A. The user selects the target that he wants to fit the parameters, and generates the corresponding QM dataset or collects the corresponding experimental measurement data. Generate the MD input file of the corresponding system and include force field information. Specify the parameters that need to be trained etc.

B. Perform initial MM simulation and calculation for the specified system and dataset, including various required property predictions.

C. Compares the initial target value calculated by MM with the QM or experimental target value, and calculates the corresponding target function and the derivatives of the target function to the training parameters according to the target type. Wherein, the target function is generally the square difference between the MM calculated value and the target value, and the detail forms are different with respect to each target property's corresponding mathematical equations. The derivative of the target function is calculated analytically using the ForceBalance method and similar equations. For different thermodynamic properties, this equation will be different.

D. According to the calculated target function and its derivative, the target function is optimized. The current algorithm used is the L-BFGS-B method to obtain the initial force field parameter value in the next iteration.

E. According to the convergence condition, judge whether the target function reaches the convergence criterion, and if so, stop the optimization iteration. If not, the next round of MM calculation is performed according to the force field parameter value of the current optimization iteration, and the target function and derivative are calculated based on this, and the target function value is optimized for subsequent iterations until convergence.

Figure 2:
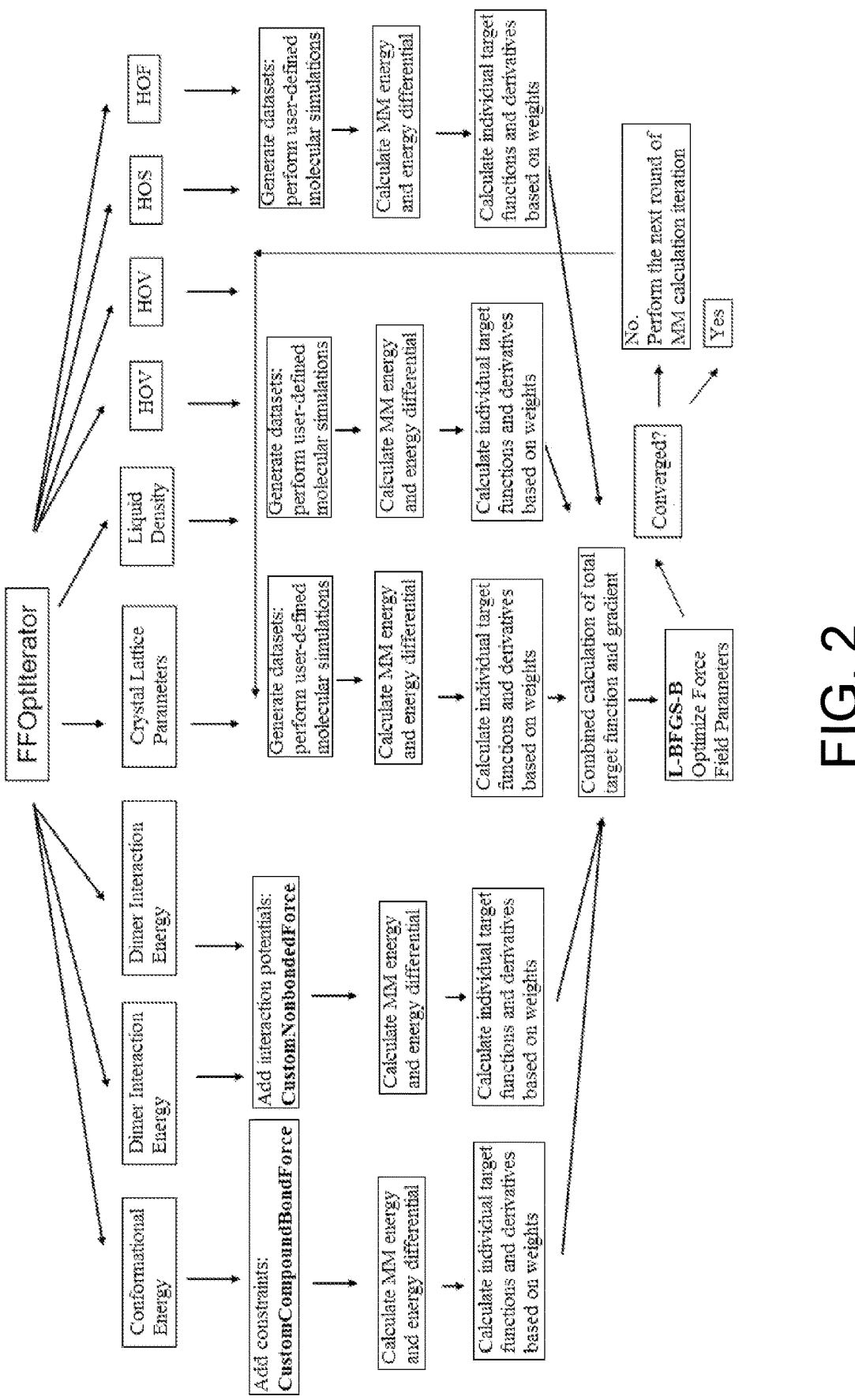
FIG. 2 is a specific operation flow and implementation of an embodiment of the present invention.

In order to ensure better code scalability, maintainability, and ease of use, the XFFOpt algorithm library is structured and divided into FFOptIterator, EnergyCalculator, and PropertyEstimator modules. The module functions as an independent and functioning in every step of the iterative optimization. The following is a brief introduction of the specific operation process and implementation of this algorithm library (FIG. 2):

Step (1): Read the initial MD input file (.prmtop, .inperd, etc.) prepared by the user, target type, training set system, configuration, QM or experimental target value, force field parameters to be trained, range of the force field parameters, etc., and use FFOptIterator module as a container to perform various parameter calculations and system preparations. The system preparations and parameter modification functions are achieved by the system editing functionality of the ParmEd object. FFOptIterator is designed to be compatible with the input of multiple molecules, crystal polymorphs, and multiple sets of training force field parameters, and includes the structure and operation in the attributes of different target types. The specific implementation method is that when the FFOptIterator object is initialized, the Python dictionary input by the user is converted into the attributes of the FFOptIterator object. The attributes are distinguished according to different target types. For different target types, different MM calculation processes and specific target functions are given, but when each attribute container returns the MM calculation value, the object and format are unified. Therefore, in the calculation of the FFOptIterator iterator, the calculated values of all target types can be unified into the sum of the target function values and the function gradient value, so that the multi-objective fitting is converted into a single-objective simulation. Therefore, the initialized FFOptIterator actually completes the system preparation work before all optimization iterations. After each round of parameter optimization, according to different target types, the class method of FFOptIterator assigns the updated force field parameters back to the ParmEd Structure object (the structure object of the ParmEd molecular editor) in each target type container of FFOptIterator. After the parameters updated, you can directly proceed to the next round of MM calculation iteration.

Step (2): Call the iterator of FFOptIterator, calculate the MM target value for the system under all target attributes, all MM energy related calculations are completed by EnergyCalculator, and call OpenMM Python API for detailed energy calculations from simulated molecular states. For conformational energy, various conformational scanning energy calculations are developed based on OpenMM's CustomCompoundForce. For dimer interaction energy, the calculation of intermolecular potential energy is developed based on CustomNonbondForce, wherein the van der Waals term uses the lorentz-berthelot combination rule. For the rest of the thermodynamic properties, use OpenMM to perform conventional NPT MD simulations. The specific simulation parameters use the settings given by the user, and it is recommended to set a long enough simulation length so that the results of each property calculation can converge. After the simulation is completed, call the PropertyEstimator to calculate the thermodynamic properties, such as volume, crystal lattice parameters, HOV, HOS, HOF, etc.

Step (3): After the systems contained in each target type system have finished the corresponding MM calculations, calculate the target function derivatives on the interested force field parameters using a formulation similar to the ForceBalance protocol. Finally, the system under all objectives is unified, combined with the set weights, and the total target function and the corresponding gradient are calculated, which are used as the input of the L-BFGS-B optimizer.

Step (4): Call the Fortran L-BFGS-B subroutine inside Scipy, use the above input to optimize the force field parameters, and perform a round of iteration. Check whether the convergence condition of the target function is reached, if not, use the updated force field parameters to edit all systems with ParmEd API, and build the next round of MM calculation inputs based on this.

Step (5): Perform the next round of MM calculation iteration, and repeat the above steps to optimize the force field parameters until the target function converges. Under normal circumstances, the number of iterations of the system with QM energy as the target is about 60 times, and the number of system convergence iterations with the objective of calculating the thermodynamic physicochemical properties is about 10 times.

Step (6): After the force field parameters being optimized and converged, visualize the output of the force field parameter files and the optimization process according to user operations. The output of parameter files is currently mainly in AMBER mol2 and frcmod formats, and subsequent system modeling in AMBER format can be directly carried out, which is very convenient for the use of MD simulation. In the visualization part, according to the target type specified by the user, the calculated target function value comparison before and after the optimization of the force field parameters can be constructed in the returned object, and the optimization iterative process of the target function, etc. can be constructed.

Embodiment1

Using Ibuprofen molecules as the system, using form 2 crystal form, dimer interaction energy dataset of 69 QM Ibuprofen-Ethanol and Ibuprofen-Water interactions produced by scanning the hydrogen bond conformation as the target, and the crystal force field is used as the initial force field to fit van der Waals parameters. The specified allowable parameter adjustment range is 10%, and each dimer pair conformation's weight is set to 1, and substituted into the XFFOpt algorithm library to complete the whole process. The target function value before optimization is 745.948 $kJ^2/mol^2$, and the target function value after optimization is 324.104 $kJ^2/mol^2$. The MM interaction energy is significantly improved compared to the QM target value RMSD.

Embodiment 2

Paracetamol molecules are used as the system, and form 1, form 2 crystal forms are used at the same time to perform force field parameter fitting of multiple polymorphs. Take the 2000 QM Paracetamol-Ethanol generated by molecular simulation conformation clustering, Paracetamol-Water interaction energy dataset, experimentally measured crystal lattice parameters, HOV, HOS, and HOF as the target, and the GAFF2 force field as the initial force field to fit van der Waals parameters. Specify the allowable parameter adjustment range as 20%, each dimer pair conformation's weight is set to 1, the weights of the crystal lattice parameters $\alpha$, $\beta$, $\gamma$ angles are set to 10, HOV, HOS, HOF's weights set to 10 and substituted into the XFFOpt algorithm library to complete the whole process. The target function value before optimization is 2.748 $kJ^2/mol^2$, and the target function value after optimization is 2.583 $kJ^2/mol^2$. This optimization degree is within the normal range of crystal-related properties, and the interaction energy of MM Dimer pairs is obviously Improved compared with the target value RMSD of QM., the calculated properties of HOV, HOS, HOF are closer to the experimental values.

Embodiment 3

Take internal case molecules as the system, adopt form 1 crystal form, and 3000 QM API-API, API-Ethanol generated by molecular simulation conformation clustering, API-Water interaction energy dataset and experimentally measured HOFs as target, taking the crystal force field as the initial force field, fitting the charge and van der Waals parameters. The specified allowable parameter adjustment range is 25%, the weight of each dimer pair conformation is set to 1, and the HOF's weight is set to 10, and substituted into the XFFOpt algorithm library to complete the entire process. The target function value before optimization is 2.797 $kJ^2/mol^2$, and the target function value after optimization is 0.548 $kJ^2/mol^2$. This optimization degree is within the normal range of crystal-related properties, and the interaction energy of MM Dimer pairs is significantly improved compared with the target value RMSD of QM. Property calculation of HOF is closer to the experimental value.

The above description is a further detailed description of the present invention in conjunction with specific preferred embodiments, and it cannot be considered that the specific implementation of the present invention is limited to these descriptions. For those of ordinary skill in the technical field to which the present invention belongs, a number of simple deductions or substitutions can be made without departing from the concept of the present invention, which should be regarded as falling within the protection scope of the present invention.

What is claimed is:

1. A working method based on a molecular force field multi-target fitting algorithm library, performed by a working system based on a molecular force field multi-objective fitting algorithm library, comprising following steps:

Step A: selecting a target of parameter fitting, generating a corresponding quantum mechanics (QM) calculated dataset or collecting a corresponding experimental data, and generating a molecular dynamics (MD) input file of a corresponding system;

Step B: performing initial molecular mechanics (MM) simulation and calculation and for a specified system and dataset;

Step C: comparing an initial target value calculated by MM with QM or experimental target value, and calculating a corresponding target function according to the target type;

Step D: using a current algorithm, optimizing the corresponding target function according to a calculated target function and its derivative to obtain an initial force field parameter value for next iteration, wherein the current algorithm is a Limited-memory Broyden-Fletcher-Goldfarb-Shanno Bound (L-BFGS-B) method;

Step E: judging whether the corresponding target function reaches a convergence criterion according to a convergence condition, if yes, stopping the optimization iteration, if not, performing a next round of MM calculation according to the force field parameter value of the current optimization iteration, and calculating the corresponding target function and derivative based on the MM calculation, and optimizing a corresponding target function value for subsequent iterations until convergence;

wherein the working system comprises:

a FFOptIterator module for input and output of system settings and training iterations for force field parameters;

an EnergyCalculator module, for MM energy and energy derivatives calculation, and calculating required values for the corresponding target functions for each iteration of an optimization algorithm;

a PropertyEstimator module, for calculating thermodynamic properties based on the MD simulation, wherein when initializing FFOptIterator and EnergyCalculator objects, user specifies the force field parameters to be trained, adjustable parameter ranges, and MD simulation parameters;

wherein the algorithm library is used for customized force field parameter training, and used for various properties dominated by intermolecular interactions; and the algorithm library is used to parameterize a specialized force field of protein-drug molecule binding and a customized force field development and verification in morphology prediction.

2. The method according to claim 1, wherein, the step A comprises a force field information, and parameters which are specified as the training parameters.

3. The method according to claim 1, wherein, in the step B, items of the initial MM simulation and calculation comprise various required property predictions.

4. A process implementation method based on a molecular force field multi-objective fitting algorithm library system, comprising:

Step (1): reading an initial molecular dynamics (MD) input file, target type, training set, system configuration, quantum mechanics (QM) or experimental value for the target dataset, force field parameters to be trained, range of the force field parameters prepared by user, and using a FFOptIterator module as a container to perform various parameter calculation and system operations;

Step (2): calling an iterator of the FFOptIterator module, calculating a molecular mechanics (MM) target value for the systems under all target attributes, performing all MM energy related calculations by an EnergyCalculator, calling an OpenMM Python application programming interface (API), for conformational energy, developing energy calculation of various conformations scan based on CustomCompoundForce of OpenMM;

Step (3): after the systems under all target attributes completed the corresponding MM calculations, calculating derivatives of the force field parameters between a corresponding target function and a ForceBalance target function in a specific form of the respective target function, and integrating the systems under all target types, combining weightings of the settings, calculating a total target function and a corresponding gradient, as an input of L-BFGS-B optimizer;

Step (4): calling a Fortran L-BFGS-B subroutine inside Scipy, using the above input to optimize the force field parameters, and performing a round of iteration, checking whether a convergence condition of the corresponding target function is reached, and if not, using updated force field parameters to edit all systems with ParmEd API, and build input metadate objects for a next round of MM calculations;

Step (5): performing the next round of MM calculation iteration, and repeating steps 1-5 to optimize the force field parameters until the corresponding target function converges;

Step (6): after the force field parameters being optimized and converged, visualizing an output of force field parameter files and optimization process according to a user operation.

5. The process implementation method according to claim 4, wherein, in the step (1), functions of the system operation and parameter modification functions are achieved by using a system editing function of ParmEd Python API, the FFOptIterator module is compatible with multi-molecules and multi-crystal polymorph type, multiple sets of training force field parameter input, and include structure and operation in attributes of different target types.

6. The workflow implementation method according to claim 4, wherein, in the step (2), for dimer interaction energy, calculation of intermolecular potential energy is developed based on CustomNonbondForce, wherein a van der Waals term adopts a lorentz-berthelot combination rule; for other the thermodynamic properties, use OpenMM to perform conventional NPT molecular dynamics simulations, specific simulation parameters use settings given by the user, and by setting a simulation length, the results of each property calculation can converge; after the simulation is completed, call PropertyEstimator to calculate the thermodynamics properties.

7. The workflow implementation method according to claim 4, wherein, in the step (5), a number of iterations of the system with a QM energy as a target is 50-100 rounds, and for the system with a calculation of thermodynamic physical and chemical properties as the target, a number of convergence iterations is 8-15 rounds.

8. The process implementation method according to claim 4, wherein, in the step (6), an output of the parameter file is in AMBER $mol^2$, frcmod format, and a visualization part is available in a returned object according to the target type specified by the user, constructing a comparison of corresponding target function values before and after the optimization of the force field parameters and the iterative process of the optimization of the corresponding target function.

\* \* \* \* \*